United States Patent
Tsuihiji et al.

(10) Patent No.: US 7,087,799 B2
(45) Date of Patent: Aug. 8, 2006

(54) AMINO GROUP CONTAINING PHENOL DERIVATIVE

(75) Inventors: Takeshi Tsuihiji, Takasaki (JP); Michiyasu Yamazaki, Takasaki (JP)

(73) Assignee: Gun Ei Chemical Industry Co., Ltd., Takasaki (JP)

(*) Notice: Subject to any disclaimer, the term of this patent is extended or adjusted under 35 U.S.C. 154(b) by 348 days.

(21) Appl. No.: 10/356,017

(22) Filed: Jan. 31, 2003

(65) Prior Publication Data

US 2003/0215734 A1 Nov. 20, 2003

(30) Foreign Application Priority Data

May 7, 2002 (JP) .................................... 2002-131686

(51) Int. Cl.
*C07C 37/045* (2006.01)
*C08C 37/00* (2006.01)

(52) U.S. Cl. ................ 568/767; 568/716; 568/717; 568/718; 568/720; 568/722; 568/723; 568/764; 528/86; 528/88; 528/93; 528/106; 528/119; 528/120; 528/121

(58) Field of Classification Search ............... 568/716, 568/717, 718, 720, 722, 723, 764, 767; 528/86, 528/88, 89, 93, 106, 119, 120, 121
See application file for complete search history.

(56) References Cited

U.S. PATENT DOCUMENTS 6,071,666 A 6/2000 Hirano et al.

FOREIGN PATENT DOCUMENTS

| EP | 0 439 362 A1 | 7/1991 |
|---|---|---|
| JP | 5-255480 A1 | 10/1993 |
| JP | 6-345866 A1 | 12/1994 |
| JP | 09-302221 | 11/1997 |
| JP | 09304924 | * 11/1997 |
| JP | 10-316636 | 12/1998 |
| JP | 11-095448 | 4/1999 |
| JP | 2002-167367 A1 | 6/2002 |

* cited by examiner

*Primary Examiner*—Sanza L. McClendon
(74) *Attorney, Agent, or Firm*—Darby & Darby

(57) ABSTRACT

An object of the present invention is to provide a material which resolves the drawbacks associated with polyimide polymers, and yet retains the advantages offered by conventional polyimide polymers.

An amino group containing phenol derivative of the present invention is represented by a general formula (1) show below, and the present invention also provides a polyimide precursor produced using such an amino group containing phenol derivative.

(1)

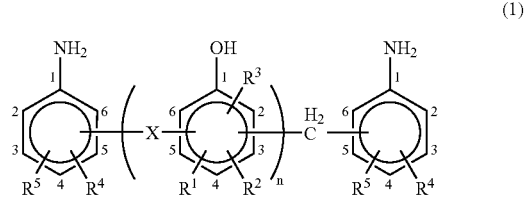

(wherein, $R^1$, $R^2$ and $R^3$, which may be the same or different, each represent an alkyl group of 1 to 9 carbon atoms, an alkoxy group of 1 to 10 carbon atoms, a COOR group (in which R represents an alkyl group of 1 to 6 carbon atoms) or a hydrogen atom; $R^4$ and $R^5$, which may be the same or different, each represent an alkyl group of 1 to 9 carbon atoms or a hydrogen atom; X represents —O—, —S—, —$SO_2$—, —$C(CH_3)_2$—, —$CH_2$—, —$C(CH_3)(C_2H_5)$—, or —$C(CF_3)_2$—; and n represents an integer of 1 or greater).

7 Claims, 9 Drawing Sheets

AMINO GROUP CONTAINING PHENOL DERIVATIVE

BACKGROUND OF THE INVENTION

1. Field of the Invention

The present invention relates to an amino group containing phenol derivative, as well as a polyimide precursor or a polyimide polymer; a photosensitive polyimide precursor or a photosensitive polyimide polymer; and a composite-material using the same.

2. Description of the Related Art

In recent years, advances in IT equipment functionality have created a demand for increased density within mobile equipment capable of processing enormous quantities of information. Furthermore, considerable focus is now being placed on the environmental impact of the materials used in the production of these types of electronic components, and the demands continue to become increasingly tight with calls for halogen free flame proofing and improved heat resistance for lead free solders and the like. Specific requirements include low stress, low dielectric constant, high heat resistance, good adhesion and good flame resistance. Furthermore polyimide polymers, which are used conventionally in electronic components for functions such as the surface protective films and interlayer insulation films of semiconductor elements, display excellent heat resistance, mechanical characteristics and flame resistance, as well as a low dielectric constant, good flame resistance, good ease of application, and good film forming properties, and as a result have been widely mooted as potential materials for next generation applications. However, current polyimide polymers have significant drawbacks including having poor adhesion (adhesiveness) with silicon wafers and metal oxide and the like, and displaying a large degree of thermal expansion following glass transition. Furthermore, modifications of polyimide polymers have proved difficult, and because such polyimide polymers are also only sparingly soluble in organic solvents, their workability is poor, and potential applications have remained comparatively limited. In order to improve on these drawbacks associated with polyimide polymers, Japanese Unexamined Patent Application, First Publication No. Hei 5-255480 discloses well balanced epoxy modified polyimide polymers which are able to maintain the inherent heat resistance of the polyimide polymer while also ensuring good flame resistance. In addition, Japanese Unexamined Patent Application, First Publication No. Hei 6-345866 discloses siloxane modified polyimide polymers in which a siloxane skeleton is introduced into the main polyimide chain in order to produce lower stress values.

However, in the epoxy modified polyimide polymers disclosed in Japanese Unexamined Patent Application, First Publication No. Hei 5-255480, the molecular weight, the ease of application and the mechanical characteristics of the polyimide polymer actually deteriorate, and the desired characteristics are not satisfactorily achieved. Furthermore, in the siloxane modified polyimide polymers disclosed in Japanese Unexamined Patent Application, First Publication No. Hei 6-345866, the heat resistance deteriorates as a result of the siloxane modification, and some loss occurs in the inherent characteristics of the original polyimide polymer. The present invention takes these issues into consideration, with an object of providing a material which resolves the drawbacks associated with conventional polyimide polymers such as poor substrate adhesion and unsatisfactory flexibility, and yet retains the advantages offered by conventional polyimide polymers.

SUMMARY OF THE INVENTION

The inventors of the present invention conducted intensive research aimed at remedying the unsatisfactory characteristics of the polyimide polymers described above, on the premise that complexes formed with other compounds may be effective in this regard. However, because conventional polyimide polymers and materials formed therefrom display poor reactivity with other compounds, this type of improvement proved extremely difficult. However on further investigation, the inventors discovered that by introducing a phenol compound into a polyimide polymer using an amino group containing phenol derivative, the formation of complexes with other compounds became possible, and the unsatisfactory characteristics of the polyimide polymer could be remedied by a complexed compound thereof, and were hence able to complete the present invention. In other words, an amino group containing phenol derivative of the present invention is an amino group containing phenol derivative represented by a general formula (1) show below.

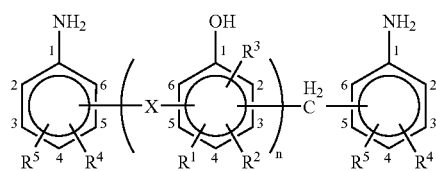

(1)

(wherein, $R^1$, $R^2$ and $R^3$, which may be the same or different, each represent an alkyl group of 1 to 9 carbon atoms, an alkoxy group of 2 to 10 carbon atoms, a COOR group (in which R represents an alkyl group of 1 to 6 carbon atoms) or a hydrogen atom; $R^4$ and $R^5$, which may be the same or different, each represent an alkyl group of 1 to 9 carbon atoms or a hydrogen atom; X represents —O—, —S—, —$SO_2$—, —$C(CH_3)_2$—, —$CH_2$—, —$C(CH_3)(C_2H_5)$—, or —$C(CF_3)_2$—; and n represents an integer of 1 or greater.)

Furthermore, a polyimide precursor of the present invention is formed from a repeating unit represented by a general formula (2) shown below.

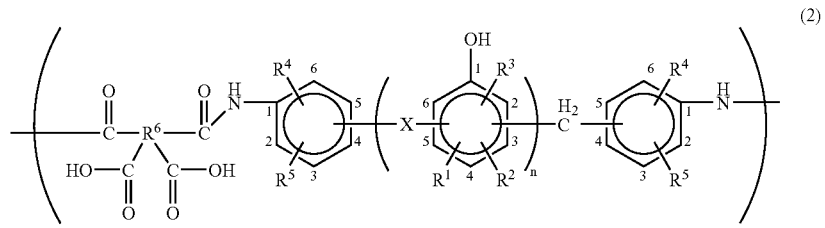

(wherein, $R^1$, $R^2$ and $R^3$, which may be the same or different, each represent an alkyl group of 1 to 9 carbon atoms, an alkoxy group of 2 to 10 carbon atoms, a COOR group (in which R represents an alkyl group of 1 to 6 carbon atoms) or a hydrogen atom; $R^4$ and $R^5$, which may be the same or different, each represent an alkyl group of 1 to 9 carbon atoms or a hydrogen atom; X represents —O—, —S—, —SO$_2$—, —C(CH$_3$)$_2$—, —CH$_2$—, —C(CH$_3$)(C$_2$H$_5$)—, or —C(CF$_3$)$_2$—; $R^6$ represents an aromatic tetracarboxylic dianhydride group; and n represents an integer of 1 or greater.)

Furthermore, a polyimide polymer of the present invention is obtained via a dehydration condensation reaction of an aforementioned polyimide precursor. Furthermore, a polyimide precursor or a polyimide polymer of the present invention may also be a photosensitive polyimide precursor or a photosensitive polyimide polymer in which a hydrogen atom of at least one phenolic hydroxyl group is substituted with a functional group which imparts photosensitivity to the polyimide precursor. In addition, a polyimide precursor or a polyimide polymer of the present invention may also be complexed with another compound to form a composite material

DETAILED DESCRIPTION OF THE PREFERRED EMBODIMENTS

Figure 1:
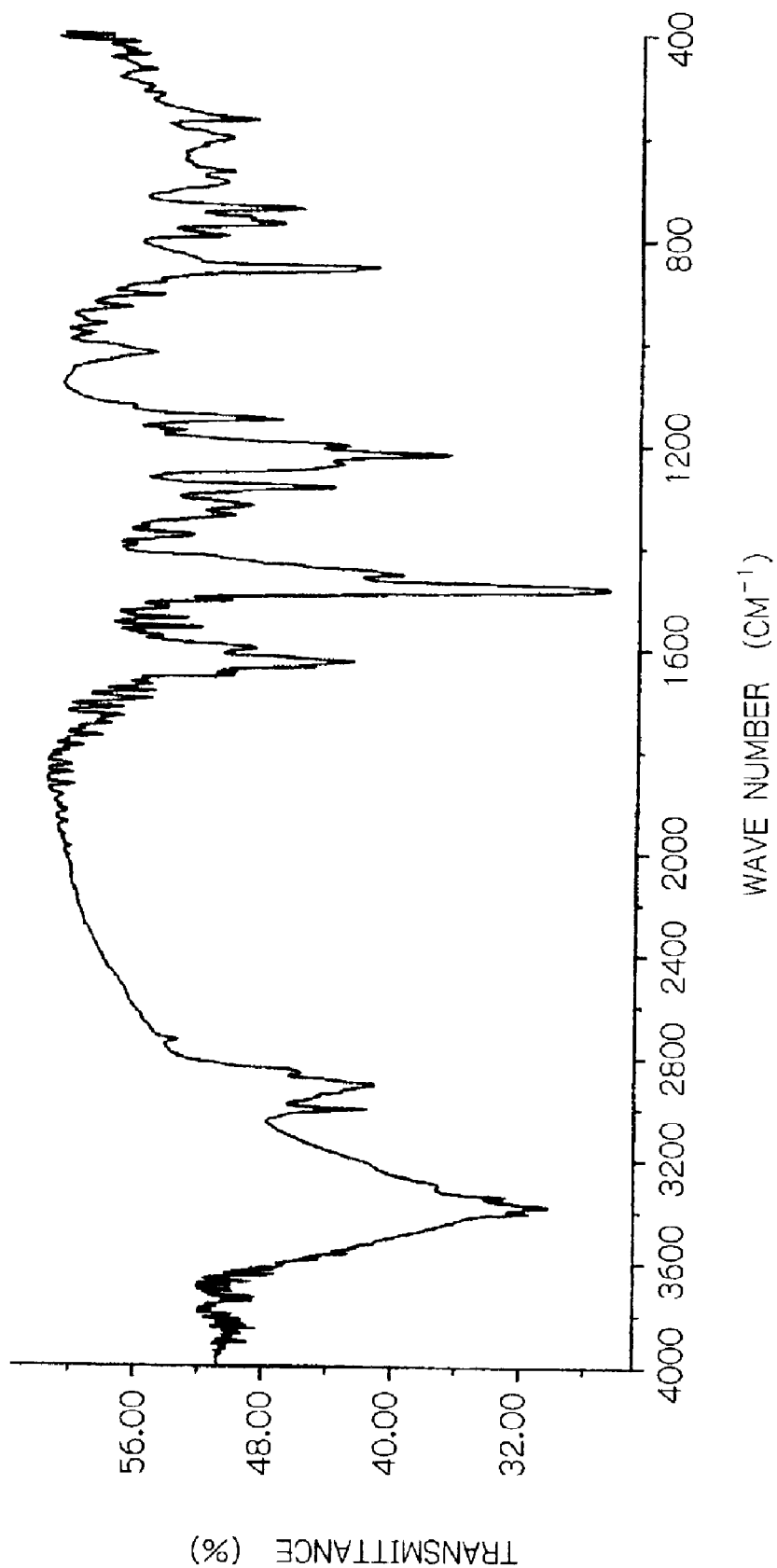
FIG. 1 is an IR spectrum of a product of a synthetic example 1.

As follows is a more detailed description of the composition of the present invention.

(A) Amino Group Containing Phenol Derivative

In an amino group containing phenol derivative according to the aforementioned general formula (1), the groups $R^1$, $R^2$ and $R^3$ within the formula represent either:

(i) a straight chain or a branched chain alkyl group of 1 to 9 carbon atoms, and preferably 1 to 4 carbon atoms;

(ii) an alkoxy group of 1 to 10 carbon atoms, and preferably 1 to 4 carbon atoms (in which the alkyl group of the alkoxy group may be either a straight chain or a branched chain);

(iii) a COOR group (in which R represents a straight chain or a branched chain alkyl group of 1 to 6 carbon atoms, and preferably 3 to 6 carbon atoms); or (iv) a hydrogen atom, and the groups $R^1$, $R^2$ and $R^3$ may be either the same or different.

Of these options, the case in which $R^1$, $R^2$ and $R^3$ represent alkyl groups enables the water resistance to be improved. In the case of alkoxy groups or COOR groups, the adhesion of the compound to a substrate can be improved, for those cases in which the compound is used in electronic components, as described below. Furthermore, in the case of COOR groups, complexing with polyesters to form composite materials also becomes possible, as described below. In addition, hydrolysis of either the alkoxy groups or the COOR groups enables the alkali solubility to be further improved, which is desirable for applications to alkali developing type uses. In other words, the groups $R^1$, $R^2$ and $R^3$ should preferably be selected in accordance with the desired application. Compounds in which either one or two of the groups $R^1$, $R^2$ and $R^3$ are hydrogen atoms, and the remainder are groups other than hydrogen atoms, display particularly preferred characteristics. Furthermore, the group or groups which are not hydrogen atoms should preferably be methyl groups. For example, combinations in which two of $R^1$, $R^2$ and $R^3$ are hydrogen atoms and one is a methyl group, or combinations in which one of $R^1$, $R^2$ and $R^3$ is a hydrogen atom and the other two are methyl groups produce improvements in moisture resistance, and are consequently preferred.

In addition, the groups $R^1$, $R^2$ and $R^3$ may be bonded to any of the carbon atom positions from 2 to 6 shown in the general formula (1), although in cases in which a regular repeating unit is required, compounds with good structural symmetry are preferred. Particularly in those cases in which two of the groups $R^1$, $R^2$ and $R^3$ are hydrogen atoms and the other one is a group other than a hydrogen atom, bonding the non-hydrogen atom group to the respective carbon atoms at position 4 generates better structural symmetry, and is consequently preferred for cases in which a regular repeating unit is required. Furthermore, if all of the groups $R^1$, $R^2$ and $R^3$ are methyl groups then the moisture resistance can be improved even further, and the solubility in solvents also improves.

The groups $R^4$ and $R^5$ represent either a straight chain or a branched chain alkyl group of 1 to 9 carbon atoms, and preferably 1 to 4 carbon atoms, or a hydrogen atom, and may be either the same or different. By introducing an alkyl group at $R^4$ and/or $R^5$ in this manner, the water resistance of the compound can be improved. Furthermore, from the viewpoint of reactivity of the amino groups, $R^4$ and $R^5$ should preferably be methyl groups.

In addition, if the $R^4$ groups, the $R^5$ groups, and the X and —CH$_2$— groups bonded to the respective benzene rings comprising the two terminal amino groups are bonded to the same number carbon atom in each case, and if the benzene rings to which the two terminal amino groups are bonded, and the —X— and —CH$_2$— groups linking these benzene rings to the benzene ring or rings to which a phenolic hydroxyl group is bonded, are symmetrical in each case, then a high molecular weight polyimide precursor can be formed, which is desirable. X represents —O—, —S—, —SO$_2$—, —C(CH$_3$)$_2$—, —CH$_2$—, —C(CH$_3$)(C$_2$H$_5$)—, or —C(CF$_3$)$_2$—, although of these, a —CH$_2$— linkage results in a simpler reaction process, and is consequently preferred. In a preferred configuration, (i) the two R$^4$ groups are each bonded to the respective carbon atom at either position 2 or position 6, (ii) the two R$^5$ groups are each bonded to the other respective carbon atom at either position 2 or position 6, and (iii) X and the methylene group are each bonded to the respective carbon atom at position 4. In such a configuration, because the hygroscopicity of the amino groups is guarded, the moisture resistance improves, and moreover because there is no interaction between the amino groups and an adjacent phenolic hydroxyl group, the reactivity of the amino group increases, which is also desirable.

n represents any integer of 1 or greater, although in actual practice is restricted to an integer of no more than 20. Furthermore, integers of 1 or greater, but no more than 15 are even more preferred. The actual value of n can be selected in accordance with the desired characteristics of the final product.

Examples of the most preferred configurations for amino group containing phenol derivatives of the present invention are shown below.

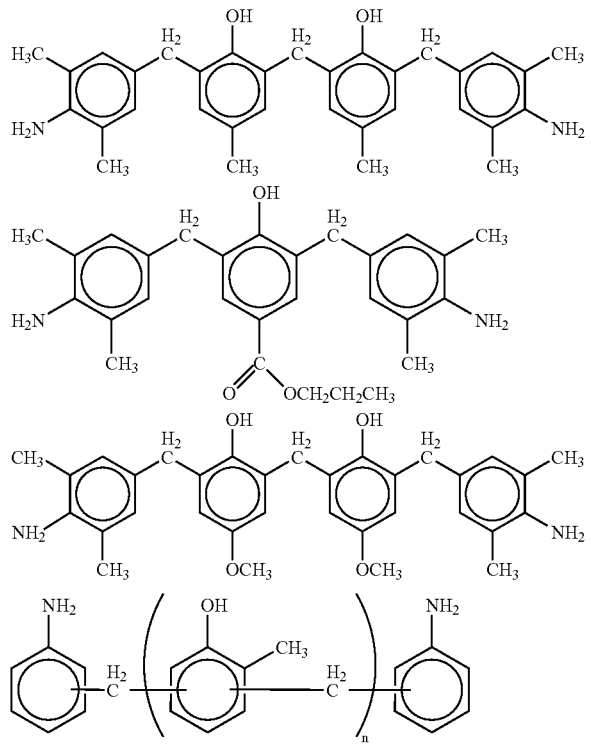

(n is preferably from 1 to 20)

A production method for an amino group containing phenol derivative of the present invention is described below for the case in which X is a —CH$_2$— group in the aforementioned general formula (1). In the production of this amino group containing phenol derivative, formalin is reacted with a phenol based compound represented by a [formula a] shown below (namely, a compound based on the general formula (1) in which the benzene rings to which the amino groups are bonded, X, and the methylene group have been excluded) and forms a dimethylolphenol derivative containing two bonded —CH$_2$OH groups, represented by a [formula b] shown below. In the general formula represented by the [formula b], if n represents a value of 2 or greater, then the structure comprises two or more phenol based compounds connected via a methylene group. The value of n can be varied depending on the characteristics of the raw material phenol based compound represented by the [formula a], and the reaction conditions. Subsequently, the two —CH$_2$OH groups of this dimethylolphenol derivative are subjected to a condensation with the amino group of an aniline derivative represented by a [formula c] shown below, yielding the amino group containing phenol derivative represented by the aforementioned general formula (1).

The groups R$^1$, R$^2$, R$^3$, R$^4$ and R$^5$, and the number n in the formulas from [formula a] through [formula c] are the same as those shown in the general formula (1), and can be appropriately selected in accordance with the desired amino group containing phenol derivative to be produced.

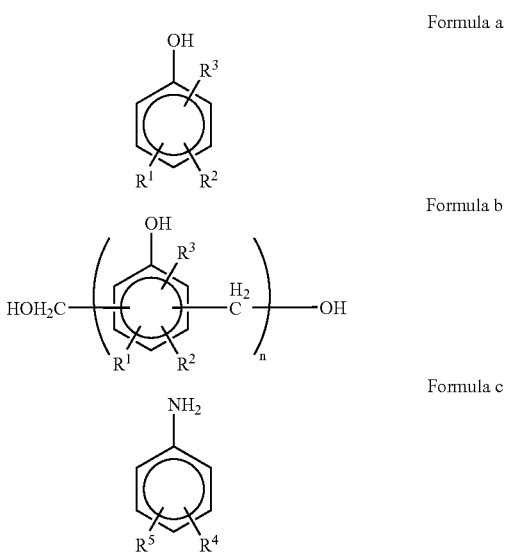

As follows is a description of a specific example of the reaction conditions. A phenol based compound and an aqueous solution of formalin (preferably with a concentration of approximately 50 mass %) containing 2 to 4 times the number of mols of the phenol based compound are placed in a reaction vessel equipped with a stirrer, a thermometer, a condenser and a dropping funnel, and with the mixture undergoing constant stirring, alkali is then added dropwise to the mixture under reaction conditions including a temperature of 0 to 50° C. and a reaction time of 1 to 2 hours. The alkali is preferably an alkali aqueous solution of sodium hydroxide or potassium hydroxide or the like, and can utilize, for example, an aqueous sodium hydroxide solution with a concentration of approximately 30 mass %. Furthermore, the quantity of alkali is typically an equivalent number of mols to the phenol based compound. After addition of the alkali, the temperature is raised, and the reaction is allowed to proceed at a reaction temperature of 20 to 80° C. for a period of 2 to 4 hours.

Subsequently, the reaction mixture is cooled, preferably to a temperature of no more than 30° C., neutralized with acid, and the product is precipitated. There are no particular restrictions on the acid used, and a suitable example is an aqueous acetic acid solution with a concentration of approximately 10 mass %. The product is then filtered, washed with water, and then dried under reduced pressure, preferably at a temperature of no more than 50° C., yielding the product (a dimethylolphenol derivative). This product, together with an aniline derivative, an acid catalyst, and where necessary an organic solvent, is then placed in a reaction vessel equipped with a thermometer, a condenser and a stirrer, and is reacted for a period of 4 to 8 hours at a temperature of 120 to 200° C., and preferably 140 to 180° C.

The quantity of the aniline derivative used should be 2 to 4 times, and preferably 2.2 to 3.0 times the number of mols of the dimethylolphenol derivative. The acid catalyst may utilize any typical organic acid or inorganic acid, and suitable examples include hydrochloric acid, paratoluenesulfonic acid and oxalic acid, although of these, oxalic acid is preferred. The quantity of the acid catalyst can be altered appropriately depending on the type of acid used, although in the case of oxalic acid, a quantity of approximately 1 mass % relative to the total quantity of the materials in a reaction vessel is preferred. Furthermore, although an organic solvent is not a necessity, using a solvent such as an alcohol, a cellosolve or toluene is preferred. The quantity of the solvent is typically from 10 to 20 mass % relative to the total quantity of the reactants. Following reaction, the mixture is cooled, and then purified where necessary using known techniques such as distillation or recrystallization, to yield an amino group containing phenol derivative according to the present invention. Examples of suitable solvents for the recrystallization include cellosolves, alcohols, acetate esters, benzene and toluene.

In those cases in which X in the aforementioned general formula (1) is a linkage group other than a —CH$_2$— group, an amino group containing phenol derivative can be produced by using a phenol based compound such as bisphenol-S, hydroxydiphenyl ether or bisphenol AF, and then performing a dimethylolation and reacting the product therefrom with an aniline derivative in the same manner as that described above.

(B) Polyimide Precursor and Polyimide Polymer

A polyimide precursor of the present invention is formed from a repeating unit represented by the aforementioned general formula (2). Furthermore, when this precursor is subjected to a dehydration condensation reaction, the two carboxyl groups and the imino group bonded to the R$^6$ group in the general formula (2) undergo respective dehydration condensations, forming ring structures and generating a polyimide polymer formed from a repeating unit represented by a general formula (3) shown below.

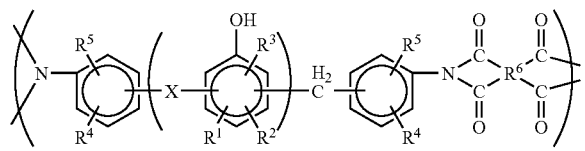

(3)

In the general formulas (2) and (3), the groups R$^1$, R$^2$, R$^3$, R$^4$, R$^5$ and X, and the number n are the same as those described for the aforementioned amino group containing phenol derivative.

In the general formulas (2) and (3), R$^6$ represents an aromatic tetracarboxylic dianhydride group. Examples of preferred aromatic tetracarboxylic dianhydrides include pyromellitic dianhydride, 3,3',4,4'-benzophenonetetracarboxylic dianhydride, 2,2',3,3'-benzophenonetetracarboxylic dianhydride, 2,3,3',4'-benzophenonetetracarboxylic dianhydride, naphthalene-2,3,6,7-tetracarboxylic dianhydride, naphthalene-1,2,5,6-tetracarboxylic dianhydride, naphthalene-1,2,4,5-tetracarboxylic dianhydride, naphthalene-1,4,5,8-tetracarboxylic dianhydride, naphthalene-1,2,6,7-tetracarboxylic dianhydride, 3,3',4,4'-diphenyltetracarboxylic dianhydride, 2,2',3,3'-diphenyltetracarboxylic dianhydride, 2,3,3',4'-diphenyltetracarboxylic dianhydride, 3,3",4,4"-p-terphenyltetracarboxylic acid, 2,2",3,3"-p-terphenyltetracarboxylic acid, 2,3,3",4"-p-terphenyltetracarboxylic acid, 2,2-bis(2,3-dicarboxyphenyl)propane dianhydride, 2,2-bis(3,4-dicarboxyphenyl)propane dianhydride, bis(2,3-dicarboxyphenyl) ether dianhydride, bis(2,3-dicarboxyphenyl)methane dianhydride, bis(3,4-dicarboxyphenyl)methane dianhydride, bis(2,3-dicarboxyphenyl)sulfone dianhydride, bis(3,4-dicarboxyphenyl)sulfone dianhydride, 1,1-bis(2,3-dicarboxyphenyl)ethane dianhydride, and 1,1-bis(3,4-dicarboxyphenyl)ethane dianhydride. Of these compounds, pyromellitic dianhydride, 3,3',4,4'-diphenyltetracarboxylic dianhydride are particularly preferred as they represent the most typical examples, and also offer low degrees of thermal expansion.

The mass average molecular weights of the polyimide precursor and the polyimide polymer fall within the same range. The mass average molecular weight of each can be appropriately adjusted in accordance with the desired application of the product, although values from 10,000 to 100,000 are preferred, and values from 20,000 to 60,000 are even more desirable. By controlling the reaction conditions, polyimide precursors or polyimide polymers according to the present invention can be produced with good control over the mass average molecular weight, to produce a value within the aforementioned range from 10,000 to 100,000, and preferably from 20,000 to 60,000. As a result, a molecular weight which compares favorably with those of conventional polyimide polymers can be achieved.

Furthermore, in addition to having a similar mass average molecular weight to conventional polyimide polymers, it was discovered that a polyimide polymer of the present invention also has the extremely useful characteristic of being soluble in organic solvents. In other words, typically, conventional aromatic polyimide polymers have been difficult to dissolve in organic solvents. As a result, typically a method is employed in which a polyimide precursor (namely a polyamic acid) which is soluble in organic solvents is prepared in advance, and a solution containing this polyimide precursor dissolved in an organic solvent is then applied to a substrate, and is subsequently converted to a polyimide by heating to cause a cyclodehydration and subsequent drying, thereby enabling the formation of a polyimide polymer film. The conditions for the heating and drying treatment steps in this method require a high temperature and a considerable length of time in order to achieve the cyclization of the polyimide precursor via a dehydration condensation and generate the product polyimide polymer. In contrast, a polyimide polymer of the present invention is soluble in organic solvents, and consequently a polyimide polymer film can be produced by applying a solution, not of a precursor, but rather of the polyimide polymer itself generated by the dehydration condensation dissolved in an organic solvent, and then performing a subsequent drying step at a far lower temperature and for a far shorter time period than the heating and drying treatment conditions described above.

Consequently, a film can be produced in a far shorter time, and via a far simpler operation than is conventionally possible. Furthermore, because only a solvent removal treatment is required, and there is no need to conduct a dehydration condensation reaction, a further benefit is obtained in that reductions in the film thickness or the generation of irregularities in the film thickness caused by dehydration do not occur.

There are no particular restrictions on the organic solvent used, provided the solvent is capable of dissolving the polyimide polymers of the present invention, and either a single solvent, or a mixture of two or more solvents may be used. Suitable solvents include organic solvents such as N-methyl-2-pyrolidone, N,N-dimethylformamide, N,N-dimethylacetamide, dimethylsulfoxide, hexamethylphosphoramide, tetramethylene sulfone, γ-butyrolactone, and p-chlorophenol, as well as glyme based solvents such as methyldiglyme and methyltriglyme.

As described above, according to the present invention, polyimide precursors and polyimide polymers can be provided which while retaining the inherent advantages of conventional polyimide polymers, also offer additional advantages in relation to film formation such as a simpler film formation process and a smoother film surface. In addition, a polyimide precursor of the present invention can be subjected to a dehydration condensation reaction and converted to a polyimide polymer, before being dissolved in a solvent, applied to a substrate, and subsequently dried to form a predetermined shape. Consequently, the problem of dehydration condensation water being generated during the heating treatment, which arises in cases where a solution of a polyimide precursor is first applied to a substrate, before being subjected to a dehydration condensation reaction, can be avoided. As a result, voids and the like, which can be generated during the-removal of water from a molded product such as a film, are less likely to occur. In thin films, water generated by the dehydration condensation reaction can readily escape into the atmosphere, but in the case of thicker films or thicker molded products in the shape of rectangular prisms or the like, the water is far more difficult to remove, and voids and the like become more likely. In these types of applications, it is preferable that a solution containing a dissolved polyimide polymer is used, as a uniform molded product with no voids can be produced. As a result, polyimide precursors and polyimide polymers of the present invention, even without mixing, offer excellent characteristics as aqueous developing materials, adhesives for electronic materials, insulating materials, and molding materials and the like.

A polyimide precursor of the present invention can be produced in the manner described below. First, an amino group containing phenol derivative and an organic solvent are placed in a reaction vessel, and the mixture is stirred for approximately 30 minutes at room temperature for example, to dissolve the amino group containing phenol derivative. There are no particular restrictions on the organic solvent provided it is capable of uniformly dissolving the materials and reactants, and either single solvents or mixtures of two or more solvents may be used. Suitable examples include organic solvents such as N-methyl-2-pyrolidone, N,N-dimethylformamide, N,N-dimethylacetamide, dimethylsulfoxide, hexamethylphosphoramide, tetramethylene sulfone, γ-butyrolactone, and p-chlorophenol, as well as glyme based solvents such as methyldiglyme and methyltriglyme. Sufficient organic solvent is used to generate a concentration of the amino group containing phenol derivative of 10 to 35 mass %, and preferably 15 to 25 mass %.

Subsequently, with the temperature maintained at no more than 30° C. (and preferably at 20 to 25° C.), an aromatic tetracarboxylic dianhydride is added gradually with constant stirring, over a period of 0.5 to 1 hour. The reaction mixture is then stirred at the same temperature for a period of 1 to 20 hours, and yields a polyimide precursor solution. In those cases in which the polyimide precursor is required, the solution should preferably be used, as is. The molar ratio of the amino group containing phenol derivative relative to the aromatic tetracarboxylic dianhydride should be within a range from 1.2 to 0.9, and preferably approximately 1, and even more preferably from 1.01 to 0.99.

In those cases in which the polyimide precursor is to be subsequently subjected to a dehydration condensation reaction to generate a polyimide polymer, the polyimide precursor solution obtained in the manner described above is heated for 2 to 4 hours at a temperature of 170 to 200° C., causing a dehydration condensation reaction and yielding a polyimide polymer.

(C) Photosensitive Polyimide Precursor and Photosensitive Polyimide Polymer

A photosensitive polyimide precursor of the present invention is a polyimide precursor formed from a repeating unit represented by the aforementioned general formula (2) in which the hydrogen atom of at least one phenolic hydroxyl group is substituted with a functional group which imparts photosensitivity to the polyimide precursor. A photosensitive polyimide polymer of the present invention is a polyimide polymer formed from a repeating unit represented by the aforementioned general formula (3) in which the hydrogen atom of at least one phenolic hydroxyl group is substituted with a functional group which imparts photosensitivity to the polyimide polymer. These photosensitive polyimide precursors and photosensitive polyimide polymers display excellent characteristics as aqueous developing materials, as solder resists for electronic materials, and as photosensitive materials. Because this type of photosensitive polyimide polymer has already undergone a dehydration condensation reaction prior to film formation, water is not generated during the film formation, which offers a considerable advantage in that the film thickness does not reduce during the film formation process. As described above for polyimide polymers of the present invention, a photosensitive polyimide polymer of the present invention is particularly effective in cases where water is difficult to remove, such as in thicker films.

When a photosensitive polyimide precursor is used in alkali developing, large quantities of photosensitive groups may need to be introduced in order to achieve appropriate contrast during the alkali developing process. In the case of a photosensitive polyimide precursor, from 10 to 90%, and preferably from 40 to 80% of the phenolic hydroxyl groups should be substituted with the aforementioned functional group which imparts photosensitivity. In the case of a photosensitive polyimide polymer, from 10 to 70%, and preferably from 20 to 40% of the phenolic hydroxyl groups should be substituted with the functional group which imparts photosensitivity.

The mass average molecular weights of the photosensitive polyimide precursor and the photosensitive polyimide polymer fall within the same range, and in order to achieve good applicability, values from 10,000 to 100,000, and preferably from 20,000 to 60,000 are preferred.

Examples of functional groups which impart photosensitivity to polyimide precursors or polyimide polymers include quinonediazide based photosensitive groups and acryloyl groups. Specific examples of preferred quinonediazide based photosensitive groups include 1,2-benzoquinonediazide-4-sulfonate esters, 1,2- naphthoquinonediazide-4-sulfonate esters, 1,2-naphthoquinonediazide-5-sulfonate esters, 2,1-naphthoquinonediazide-4-sulfonate esters, and 2,1-naphthoquinonediazide-5-sulfonate esters.

As an example, a photosensitive polyimide precursor of the present invention substituted with a quinonediazide based photosensitive group can be produced by preparing a polyimide precursor of the present invention using the method described above, and then reacting 100 parts by mass of this precursor with preferably 1 to 50 parts by mass, and even more preferably 5 to 25 parts by mass of quinonediazide sulfonyl chloride. In this reaction, it is preferable that following the addition of the quinonediazide sulfonyl chloride, an additional 1.2 equivalents of triethylamine is added dropwise over a period of approximately 30 minutes, at a temperature of no more than 30° C., and preferably no more than 25° C., and is subsequently reacted for a period of 2 to 12 hours. Subsequently, the reaction mixture is poured into a large volume of a 0.2% aqueous oxalic acid solution, equivalent to 10 times the volume of the reaction solution, and the precipitated solid fraction is filtered, washed with ion exchange water and then dried to yield the photosensitive polyimide precursor. In addition, a photosensitive polyimide polymer of the present invention substituted with a quinonediazide based photosensitive group, for example, can be produced in a similar manner to that described above, by first preparing a polyimide polymer of the present invention, and then reacting this resin with quinonediazide sulfonyl chloride in a similar manner to the aforementioned photosensitive polyimide precursor. Furthermore, a photosensitive polyimide polymer can also be produced by subjecting an aforementioned photosensitive polyimide precursor to a dehydration condensation reaction. A photosensitive polyimide precursor or a photosensitive polyimide polymer substituted with an acryloyl group can be produced in the same manner as that described above, with the exception of replacing the quinonediazide sulfonyl chloride with acrylyl chloride.

Although dependent to some degree on the desired final application of the product, the most preferred photosensitive polyimide precursors and photosensitive polyimide polymers are those which use a preferred amino group containing phenol derivative shown in the above:

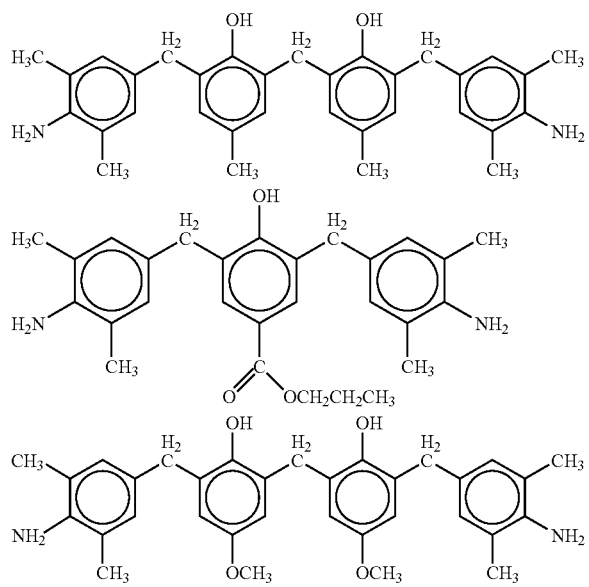

-continued

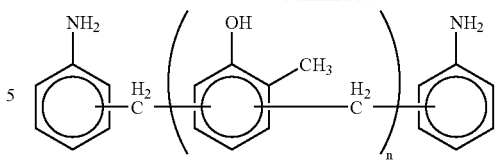

(n is preferably from 1 to 20). Of these, precursors and resins which utilize pyromellitic dianhydride or 3,3',4,4'-diphenyltetracarboxylic dianhydride as the aromatic tetracarboxylic dianhydride are particularly preferred for those applications in which the effects of thermal expansion are an important factor.

(D) Composite Materials

Polyimide precursors and polyimide polymers of the present invention can be converted to composite materials by complexing with other compounds. In the present invention, there are no particular restrictions on these other compounds used in the formation of composite materials provided they contain a functional group capable of reacting with a phenolic hydroxyl group, and although the nature of the compound will vary depending on the application, synthetic resins and the like are preferred. Specific examples include epoxy resins, silicone resins and acrylic resins, and these resins may be used singularly, or in mixtures of two or more different resins. In the present invention, composite materials formed with epoxy resins or silicone resins can provide additional favorable characteristics such as increased heat resistance, improved mechanical characteristics, electrical insulation and flame resistance of the polyimide polymer, as well as good film moldability, which are particularly desirable in electronic component applications such as surface protective films for semiconductor elements and interlayer insulation films and the like. Furthermore, in those cases in which any one of the groups $R^1$, $R^2$ and $R^3$ in the general formulas (2) and (3) is a COOR group, composite materials can also be formed with polyester resins. Of the polyimide precursors and the polyimide polymers, complexing is possible for any precursor or resin which has at least one phenolic hydroxyl group, and consequently complexing is also possible for photosensitive polyimide precursors or photosensitive polyimide polymers with at least two phenolic hydroxyl groups, where a portion of the hydrogen atoms of these hydroxyl groups have been substituted with a quinonediazide based photosensitive group.

A composite material can be produced using the sample method described below. First, a polyimide precursor or a polyimide polymer of the present invention and a compound for forming the composite material are mixed uniformly. In the case of a compound such as an epoxy resin with a glycidyl group, mixing is conducted for a period of 20 to 60 minutes, and preferably approximately 30 minutes, at a temperature of 40 to 80° C., and preferably a temperature of approximately 60° C. Subsequently, a catalyst such as triphenylphosphine, triethylamine or any other typical curing accelerator (although triphenylphosphine is preferred) is added, and the mixture is stirred for 20 to 60 minutes, and preferably for approximately 30 minutes, at a temperature of 40 to 80° C., and preferably a temperature of approximately 60° C., to cause the complexing reaction to proceed. The temperature is then raised to 170 to 350° C., and that temperature is maintained for 3 to 5 hours to cure the material and produce the composite material. The curing can be conducted by, for example, maintaining a temperature of 180° C. for one hour, raising the temperature and then maintaining a temperature of 250° C. for a further one hour, and then raising the temperature again and maintaining a temperature of 320° C. for yet another one hour. In those cases where a film is to be formed, the composite material can be applied to a substrate surface using spin coating or the like, prior to the temperature raising and curing steps, and the material can then be cured under similar conditions to those described above, enabling a substrate bonded film to be produced with considerable ease.

The relative proportions of the polyimide precursor or polyimide polymer of the present invention and the other compound during the production of a composite material can be altered appropriately in accordance with the nature of the other compound used and the intended final application, although in the case of the production of a composite material with a synthetic resin for example, ratios (mass ratios) within a range from 10:1 to 1:10, and preferably from 4:1 to 1:4 are used.

In the case of complexing with an epoxy resin, there are no particular restrictions on the type of epoxy resin, which can be selected in accordance with the desired final application. Examples of suitable epoxy resins include phenol novolak type epoxy resins; o-cresol novolak type epoxy resins; epoxides of bisphenol A, bisphenol S, bisphenol F and biphenol and the like; and glycidylamine type epoxy resins formed by reaction of a polyamine such as diaminophenylmethane and epichlorohydrin, and these resins may be used singularly, or in combinations of two or more such resins. For example, in the case of an application to a molding material, any of the various novolak resins are preferred, whereas in the case of applications to films or adhesives, dimer type epoxy resins using the various bisphenols are preferred. The epoxy equivalence of the epoxy resin can be varied in accordance with the intended application, although typical values are from 150 to 250, and preferably from 160 to 200. Composite materials formed by complexing an epoxy resin display a surprisingly large increase in the glass transition point over the glass transition point of the polyimide precursor prior to complexing, and the improvement in heat resistance is marked. Accordingly, a material can be produced which not only has good adhesion to electronic components such as substrates, but also displays extremely good heat resistance.

For applications to electronic components, the epoxy resin should preferably be selected from resins conventionally used in electronic component applications. In such cases, the relative proportions of the polyimide precursor or polyimide polymer of the present invention and the epoxy resin are typically within a range from 4:1 to 1:4, and preferably from 2:1 to 1:2 (mass ratios). Furthermore recently, film like materials have been proposed as IC sealing materials, and because composite materials of the present invention display the excellent film formation properties of a polyimide polymer, they can also be ideally applied to this type of application.

In the case of complexing with a silicone resin, there are no particular restrictions on the type of silicone resin, which can be selected in accordance with the desired final application. The number average molecular weight of the silicone resin can be altered in accordance with the intended application, although typical values are within a range from 3,000 to 30,000, and preferably from 5,000 to 20,000. Recently, with the increasing degree of integration in electronic components, silicone resins are being used as low stress resins. Accordingly, by complexing a silicone resin, a film or the like can be produced which offers good flexibility and low stress, and also displays the favorable characteristics of a polyimide polymer, namely a high level of heat resistance, a favorable dielectric constant and good film forming properties. In particular, the composite material has the favorable film forming properties of a polyimide polymer, and also exhibits the flexibility of a silicone resin, and consequently is ideal for applications such as film like sealing materials and flexible printed circuit boards. In such cases, the silicone resin should preferably be selected from resins conventionally used in electronic component applications. Suitable examples include phenylmethyl silicone resin, methyl silicone resin and modified silicone resin. In such cases, the relative proportions of the polyimide precursor or polyimide polymer of the present invention and the silicone resin are typically within a range from 10:10 to 10:1, and preferably from 10:4 to 10:2 (mass ratios).

In this manner, by forming a polyimide precursor or a polyimide polymer using an amino group containing phenol derivative of the present invention, the introduction of a phenolic hydroxyl group enables composite materials to be formed by complexing with other materials, while the favorable polyimide polymer characteristics such as heat resistance, mechanical characteristics, electrical insulation and flame resistance can be retained. What is described here as complexing refers to a reaction of an aforementioned phenolic hydroxyl group of an amino group containing phenol derivative group with a functional group of another compound, resulting in bond formation. Complexing with another resin enables the favorable characteristics of this other resin to be imparted to the composite material. Specifically, complexing with an epoxy resin results in a material with a low thermal expansion coefficient and good adhesion to substrates such as glass, metals and metal oxides. In contrast, complexing with silicone resins provides a material which offers good adhesion to silicon wafers and glass plates, and also displays excellent flexibility. Furthermore, in a polyimide precursor or a polyimide polymer using an amino group containing phenol derivative of the present invention, the hydrogen atoms of phenolic hydroxyl groups can be substituted with a functional group which imparts photosensitivity to the polyimide precursor or polyimide polymer, enabling the preparation of a photosensitive polyimide precursor or a photosensitive polyimide polymer.

EXAMPLES

As follows is a more detailed description of the present invention based on a series of examples.
(Synthesis of Amino Group Containing Phenol Derivatives)

Synthetic Example 1
(1) Synthesis of a Dimethylolphenol Derivative
2,2'-methylenebis(4-methyl-6-hydroxymethylphenol) shown below was synthesized as a dimethylolphenol derivative, in the manner described below.

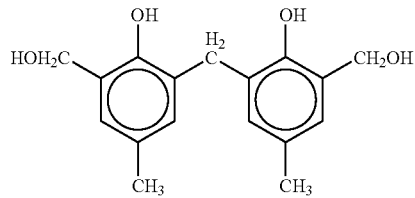

162 g of p-cresol and 360 g of a 50% aqueous formalin solution were placed in a 2 L four neck flask equipped with a thermometer, a condenser, a stirrer and a dropping funnel.

200 g of a 30 mass % aqueous solution of NaOH was then added dropwise over a two hour period at a temperature of no more than 30° C. The temperature was then raised to 60° C. and the mixture was reacted for 4 hours, before the temperature was once again cooled to a temperature of no more than 30° C. 900 g of a 10 mass % aqueous acetic acid solution was then added dropwise to neutralize the reaction mixture, which precipitated a crude product. This crude product was filtered, washed with water (300 g of water was used for each wash, and four separate washing operations were performed), and then dried under reduced pressure at a temperature of less than 50° C. (approximately 40° C.) to yield the product. The yield was 200 g, and the product was a white powder.

(2) Synthesis of an Amino Group Containing Phenol Derivative

Using the product obtained above, 2,2'-methylenebis{4-methyl-6-(3,5-dimethyl-4-aminobenzyl)phenol} shown below was synthesized as an amino group containing phenol derivative, in the manner described below.

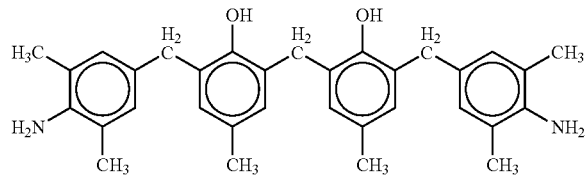

First, 200 g of the above product, 190 g of 2,6-dimethylaniline, 3.0 g of oxalic acid, and 20 g of ethylcellosolve were placed in a 500 ml four neck flask equipped with a thermometer, a condenser, and a stirrer, and reacted for 4 hours at a temperature of 120° C. The reaction mixture was then cooled and recrystallized from 800 g of ethylcellosolve to yield the amino group containing phenol derivative. The yield was 315 g, and the product was a pale yellow power. Identification of the compound was performed based on the mass spectrum, the IR spectrum, and the melting point. The melting point was measured using a DSC 220 manufactured by Seiko Instruments Inc., on a sample size of 3 to 5 mg, using a temperature range of 20 to 550° C., and raising the temperature at a rate of 10° C./min. The IR spectrum is shown in FIG. 1. The melting point for the product was 201° C.

Synthetic Example 2

(1) Synthesis of a Dimethylolphenol Derivative 2,6-dihydroxymethyl-4-n-propylcarboxyphenol shown below was synthesized.

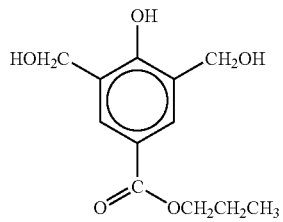

With the exception of altering the conditions described below, a product was obtained using the same method as described in the synthetic example 1. The product yield was 100 g of a white powder.

Initial reactants: 90 g of propyl p-hydroxybenzoate and 120 g of a 50 mass % aqueous formalin solution.

Dropwise addition conditions: 67 g of a 30 mass % aqueous solution of NaOH added over a two hour period at a temperature of no more than 40° C.

Raised temperature reaction conditions: 3 hours at 75° C.

Neutralization conditions: 540 g of a 10 mass % aqueous acetic acid solution.

(2) Synthesis of an Amino Group Containing Phenol Derivative

Using the product obtained above, 2,6-bis(3,5-dimethyl-4-aminobenzyl)-4-n-propylcarboxyphenol) shown below was synthesized as an amino group containing phenol derivative.

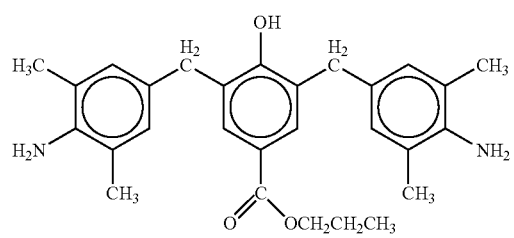

Figure 2:
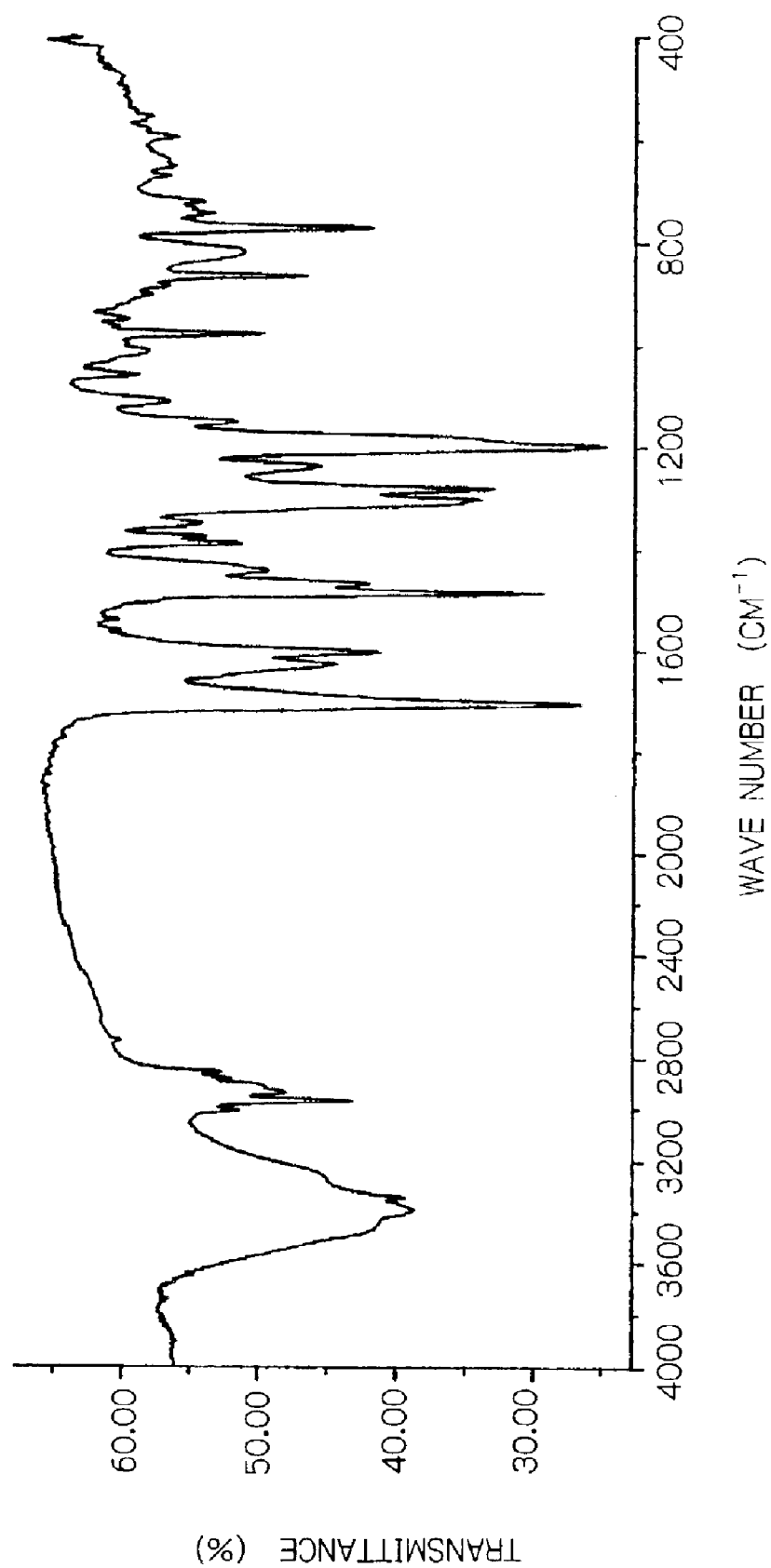
FIG. 2 is an IR spectrum of a product of a synthetic example 2.

With the exception of altering the conditions described below, a product was obtained using the same method as described in the synthetic example 1. The product yield was 125 g of a pale yellow power. The IR spectrum is shown in FIG. 2. Furthermore, the melting point of the product was 127.8° C.

Initial reactants: 72 g of the above product, 80 g of 2,6-dimethylaniline, and 1.5 g of oxalic acid Reaction conditions: 4 hours at 140° C.

Synthetic Example 3

(1) Synthesis of a Dimethylolphenol Derivative 2,6-dihydroxymethyl-4-t-butylphenol shown below was synthesized as a dimethylolphenol derivative.

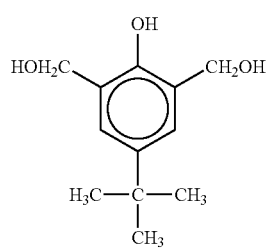

With the exception of altering the conditions described below, a product was obtained using the same method as described in the synthetic example 1. The product yield was 67 g of a reddish yellow powder.

Initial reactants: 61 g of p-methoxyphenol and 162 g of a 37 mass % aqueous formalin solution.

Dropwise addition conditions: 67 g of a 30 mass % aqueous solution of NaOH added over a two hour period at a temperature of no more than 40° C.

Raised temperature reaction conditions: 2 hours at 60° C.

Neutralization conditions: 540 g of a 10 mass % aqueous acetic acid solution.

(2) Synthesis of an amino group containing phenol derivative

Using the product obtained above, 2,6-bis(3,5-dimethyl-4-aminobenzyl)-4-t-butylphenol) shown below was synthesized as an amino group containing phenol derivative.

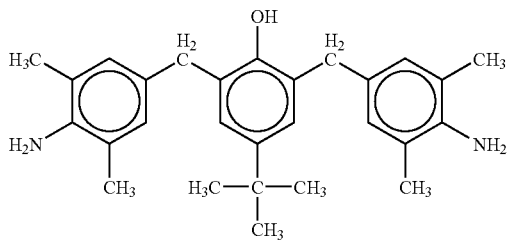

Figure 3:
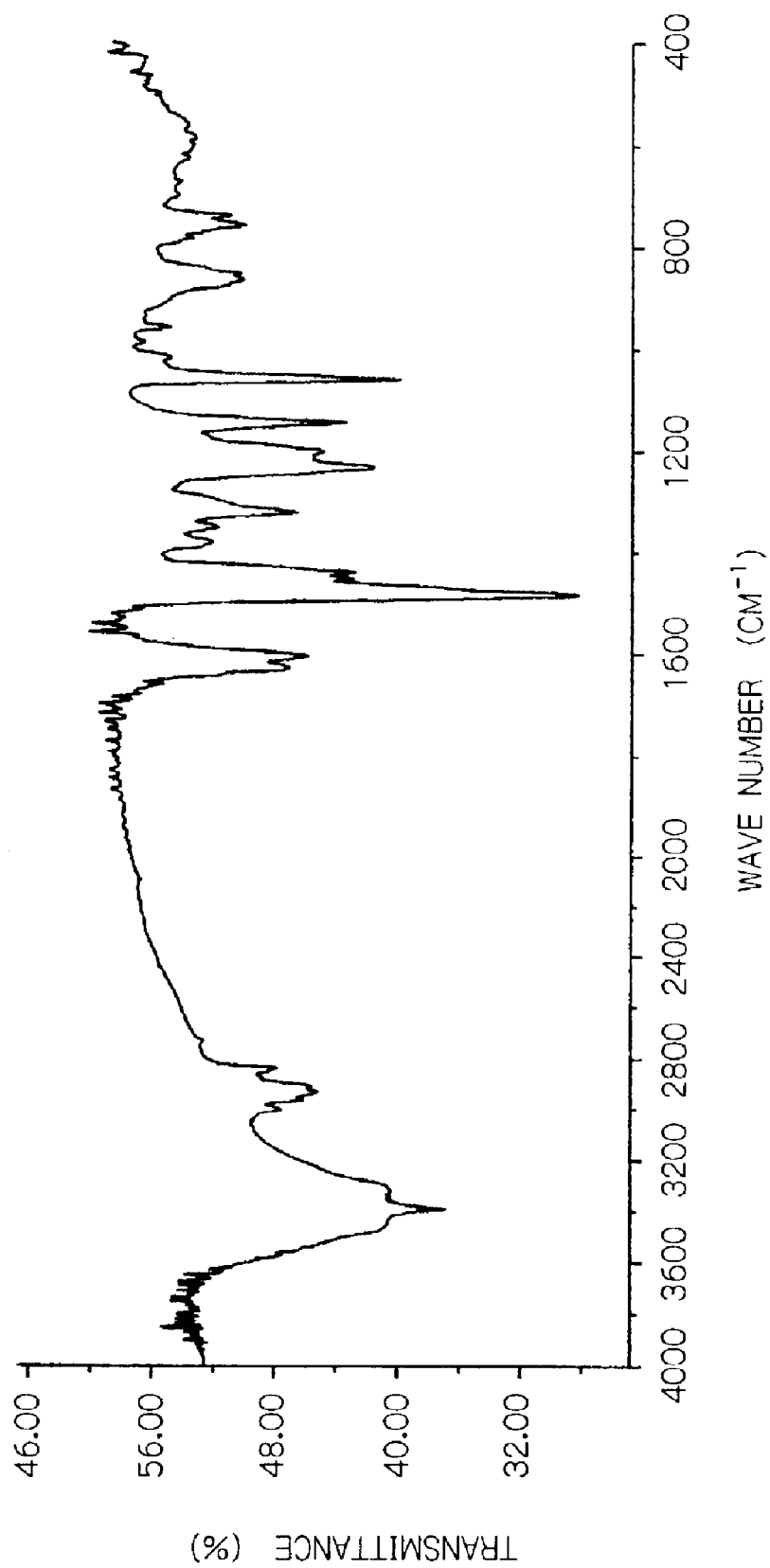
FIG. 3 is an IR spectrum of a product of a synthetic example 3.

With the exception of altering the conditions described below, a product was obtained using the same method as described in the synthetic example 1. The product yield was 120 g of a pale red solid. The IR spectrum is shown in FIG. 3. Furthermore, the melting point of the product was 180.7° C.

Initial reactants: 32 g of the above product, 30 g of 2,6-dimethylaniline, and 0.6 g of oxalic acid Reaction conditions: 4 hours at 140° C.

Purification (recrystallization) conditions: 150 g of ethylcellosolve.

Synthetic Example 4

(1) Synthesis of a Dimethylolphenol Derivative

A resol type orthocresol resin shown below was prepared as a dimethylolphenol derivative.

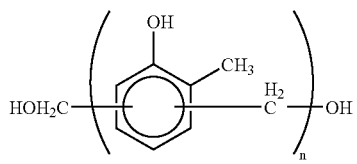

With the exception of altering the conditions described below, a product was obtained using the same method as described in the synthetic example 1. The product yield was 100 g of a brown, viscous liquid.

Initial reactants: 81 g of o-cresol and 99 g of a 50 mass % aqueous formalin solution.

Dropwise addition conditions: 100 g of a 30 mass % aqueous solution of NaOH added over a two hour period at a temperature of no more than 30° C.

Raised temperature reaction conditions: 1 hour at 70° C.

Neutralization conditions: 450 g of a 10% aqueous acetic acid solution.

(2) Synthesis of an Amino Group Containing Phenol Derivative

An orthocresol novolak with an aminobenzyl group at both terminals shown below was synthesized as an amino group containing phenol derivative.

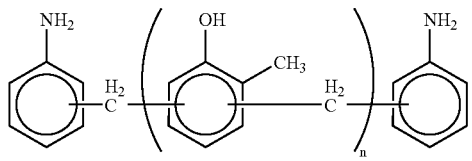

Figure 4:
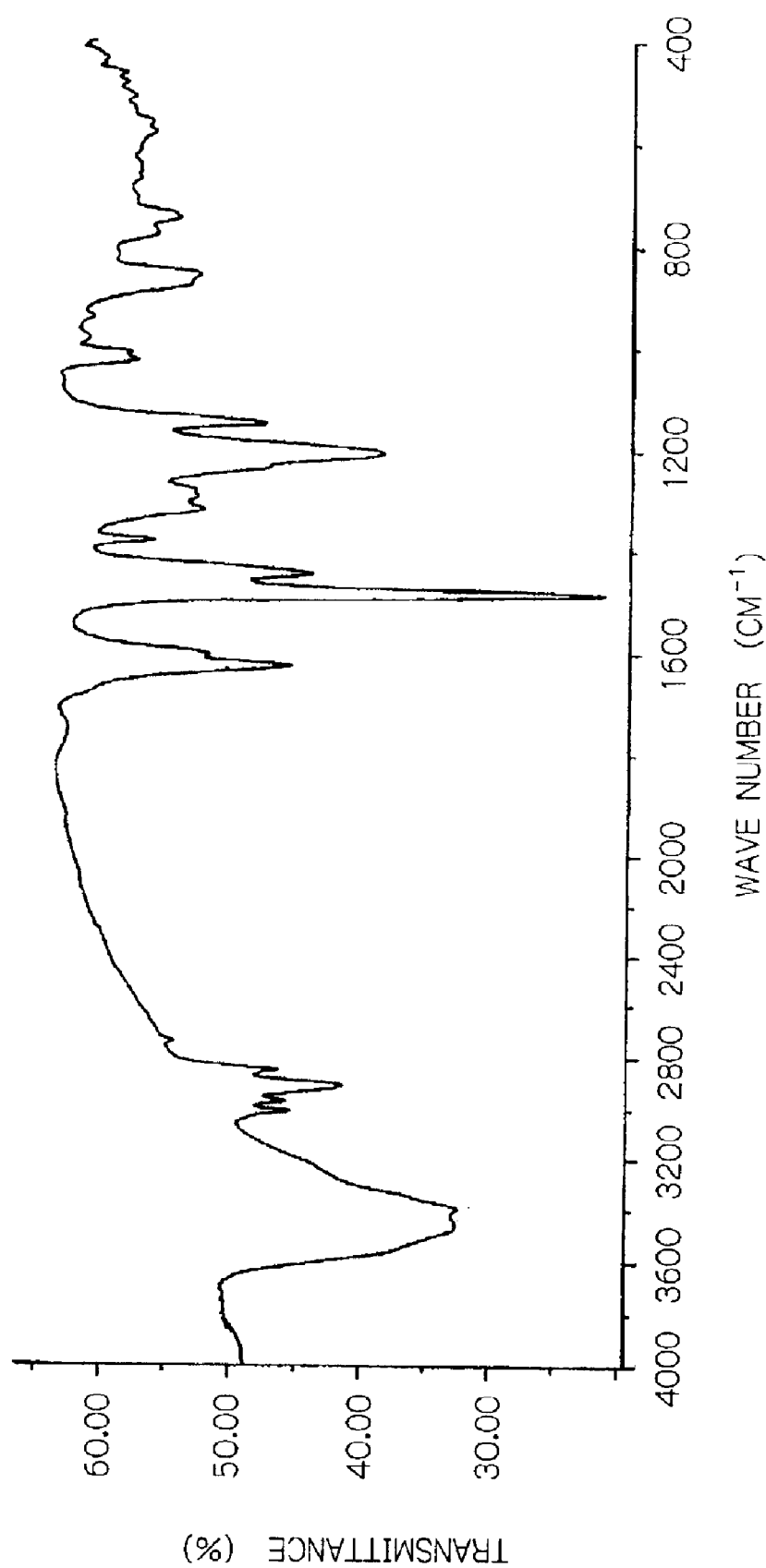
FIG. 4 is an IR spectrum of a product of a synthetic example 4.

First, 100 g of the above product, 180 g of aniline, and 2.8 g of oxalic acid were placed in a 500 ml four neck flask equipped with a thermometer, a condenser, and a stirrer, and reacted for 4 hours at a temperature of 180° C. Any unreacted reactants were then removed over a 30 minute period at −720 mmHg and 180° C. The product was then removed and yielded 250 g of a brown solid. The softening point was 113° C. The IR spectrum is shown in FIG. 4. Furthermore, measurement of the mass average molecular weight by GPC (gel permeation chromatography) revealed a value of 770.

(Synthesis of a Polyimide Precursor)

Synthetic Example 5

Using the amino group containing phenol derivative obtained in the synthetic example 1, a polyimide precursor was synthesized in the manner described below.

Figure 5:
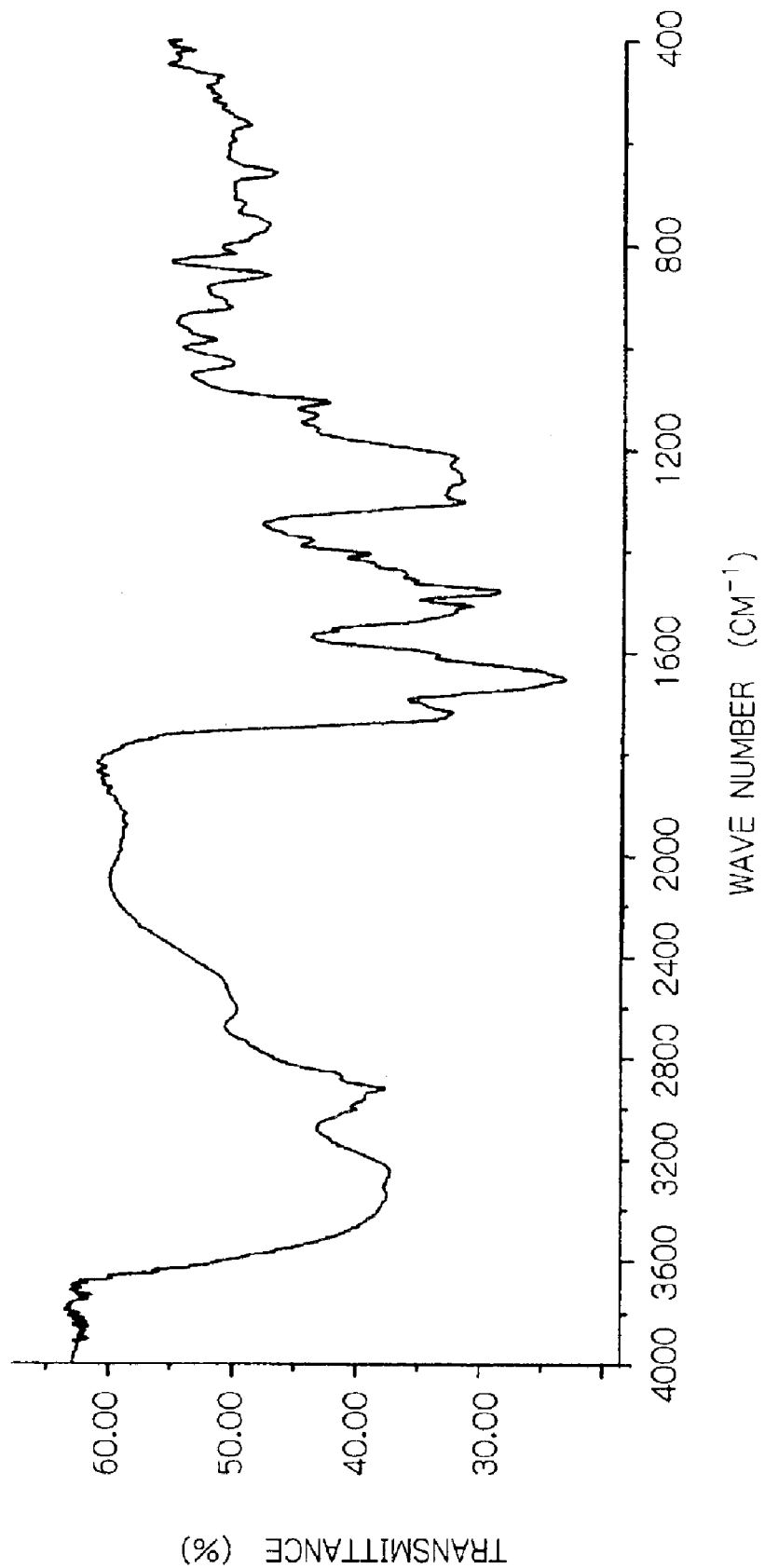
FIG. 5 is an IR spectrum of a product of a synthetic example 5.

4.940 g of the amino group containing phenol derivative obtained in the synthetic example 1 and 40.30 g of NMP solvent (N-methylpyrolidone) were placed in a reaction vessel, and the amino group containing phenol derivative was dissolved by stirring for 30 minutes at room temperature. Subsequently, 2.180 g of pyromellitic dianhydride was added at a temperature of no more than 30° C., and the reaction mixture was then stirred for 24 hours at a temperature of 25 to 28° C. to yield a polyimide precursor. The IR spectrum is shown in FIG. 5. The mass average molecular weight of the product was 34,500.

(Synthesis of a Polyimide Varnish)

Synthetic Example 6

Using the amino group containing phenol derivative obtained in the synthetic example 4, a polyimide varnish (a polyimide polymer solution) was synthesized in the manner described below.

Figure 6:
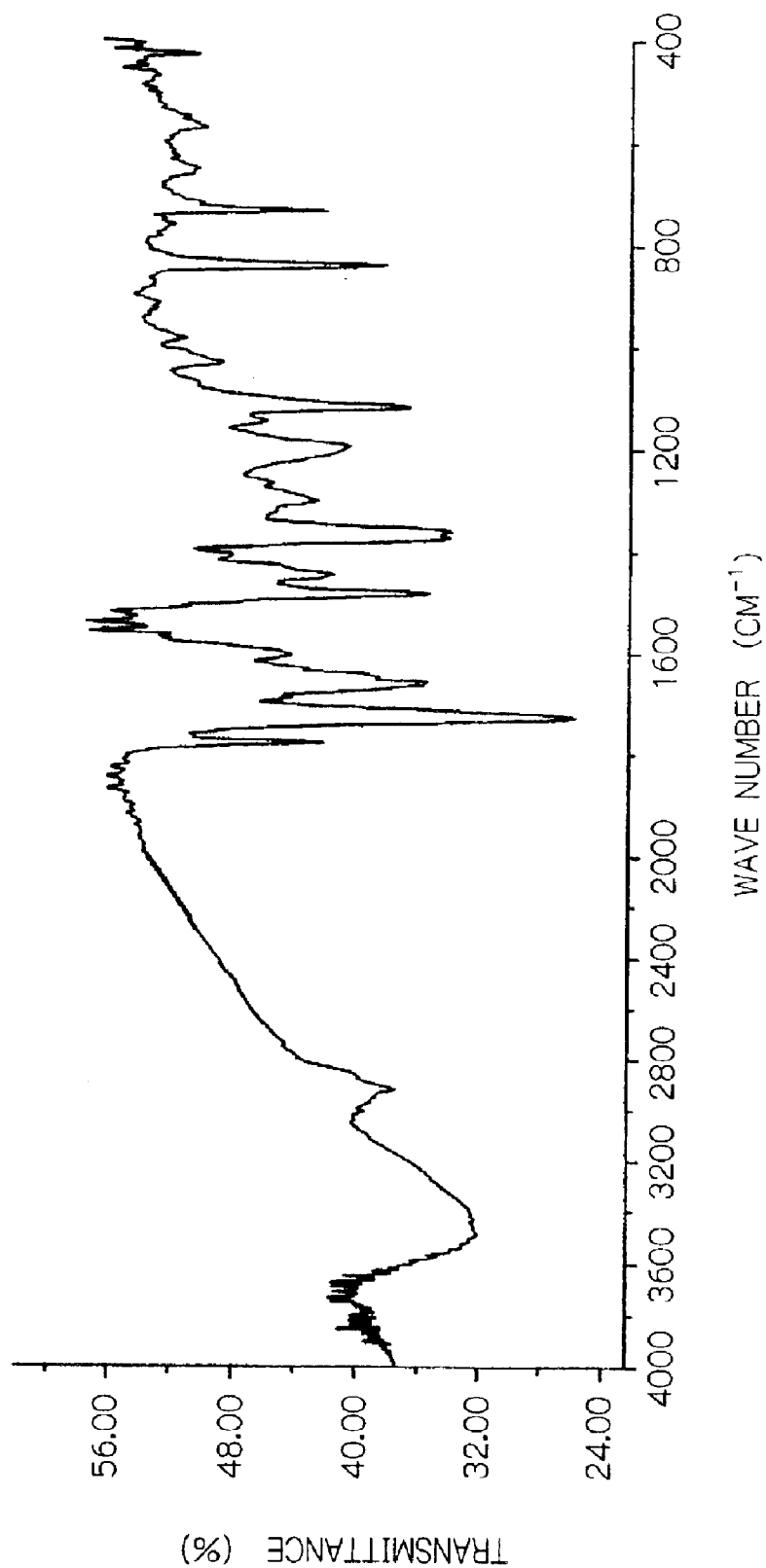
FIG. 6 is an IR spectrum of a product of a synthetic example 6.

6.180 g of the amino group containing phenol derivative obtained in the synthetic example 4 and 32.57 g of NMP solvent were placed in a reaction vessel, and the amino group containing phenol derivative was dissolved by stirring for 30 minutes at room temperature. Subsequently, 2.180 g of pyromellitic dianhydride was added at a temperature of no more than 30° C., and the reaction mixture was stirred for one hour. Under an atmosphere of nitrogen, the temperature was then gradually raised to 180° C. over a one hour period, and a dehydration condensation reaction (a cyclodehydration) was then performed over a 3 hour period to yield a polyimide varnish. The IR spectrum of the product is shown in FIG. 6. Furthermore, the mass average molecular weight of the product was 32,000.

(Synthesis of a Polyimide Precursor for Use in a Comparative Example 2, Described Below)

Synthetic Example 7

Using 4.00 g of p,p'-methylenedianiline, 4.36 g of pyromellitic dianhydride and 47.3 g of NMP solvent, a polyimide precursor was prepared using the same method as that described for the synthetic example 5.

(Synthesis of a Polyimide Precursor for use in a Comparative Example 3, Described Below)

Synthetic Example 8

20.0 g (0.10 mol) of p,p'-methylenedianiline and 6.00 g (0.001 mol) of α,ω-bis(3-aminopropyl)polydimethylsiloxane with a mass average molecular weight of 6000 were dissolved in 272 g of NMP solvent, 22.02 g (0.101 mol) of pyromellitic dianhydride was added, and the mixture was reacted for 24 hours to yield a polyimide precursor.

Example 1

Figure 7:
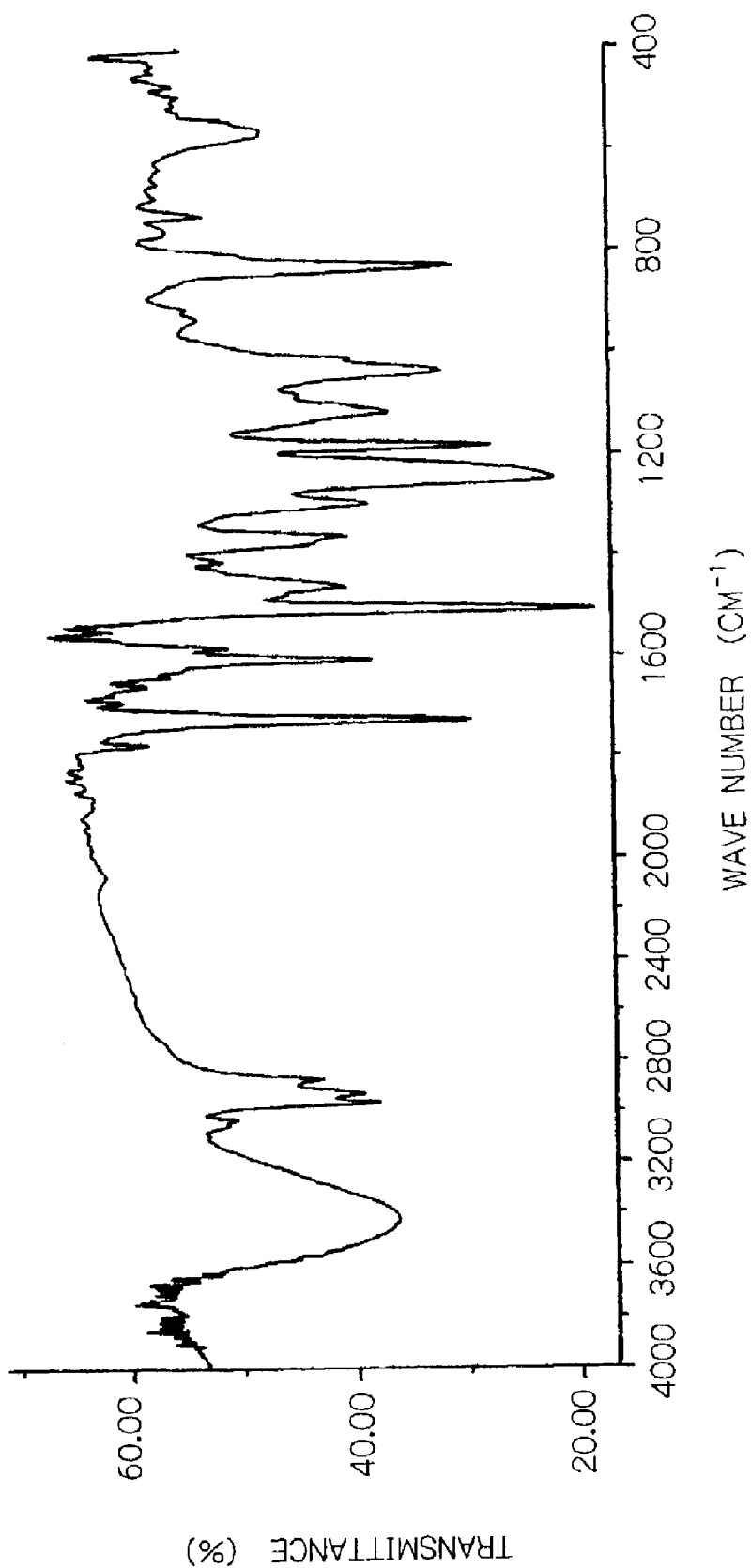
FIG. 7 is an IR spectrum of a product of an example 1.

Complexing of the Polyimide Precursor of Synthetic Example 5 and an Epoxy Resin 10 g of an epoxy resin (Epikote 828 (a brand name of Yuka Shell Epoxy Co., Ltd.)) and 50 g of the polyimide precursor produced in the synthetic example 5 were mixed for 30 minutes at 60° C. to produce a uniform mixture, and 0.1 g of triphenylphosphine was then added as a catalyst, and the mixture was stirred for a further 30 minutes at 60° C. The thus obtained composite polyimide precursor solution was applied to a silicon wafer and a Cu substrate using spin coating techniques, and then subjected to heat treatment for 1 hour at 180° C. and 1 hour at 250° C., to yield polyimide-epoxy complexed polymer film. The IR spectrum of this polyimide film is shown in FIG. 7. The polyimide film coated silicon wafer was then subjected to 48 hours of heat treatment in a pressure cooker at a temperature of 121° C. and 100% RH, and a cross cut peeling test was performed both prior to, and following this heat treatment (in Table, these results are recorded as "pre PCT" and "post PCT" respectively). The results revealed that peeling did not occur, and that a good level of adhesion was maintained. The aforementioned cross cut peeling test is performed by using a cutter to cut the film into 100 separate 5 mm×5 mm squares, sticking a cellophane adhesive tape to the film, and then pulling away the cellophane and recording the number of squares which are peeled away with the cellophane. The same test was also performed using the Cu substrate sample. The results are shown in Table 1.

The glass transition point, the thermal decomposition temperature (differential scanning calorimetry [DSC]), and the coefficient of linear thermal expansion were also measured for the above product, using the techniques outlined below. The aforementioned composite polyimide precursor solution was applied to aluminum foil by roll coating, and following heat treatment, was peeled off the aluminum foil to yield a film of thickness 50 μm. The glass transition point and the coefficient of linear thermal expansion were measured using this film. Specifically, the measurements were performed using a TMA (brand name, manufactured by SII), under conditions including a temperature of 200 to 400° C., a rate of temperature increase of 2° C./min., a loading of 10 g. The thermal decomposition temperature was measured using a TG/DTA 320 (brand name, manufactured by SII), under conditions including a sample size of 10 mg, a temperature of 100 to 800° C., and a rate of temperature increase of 10° C./min.

For the purposes of comparison, the polyimide precursor produced in the synthetic example 7 was combined in a 1:1 ratio (mass ratio) with the epoxy resin used in the example 1, and then complexed in the same manner as described in the example 1, and the resulting product was subjected to the same tests as above (comparative example 1). Furthermore, the same tests were also performed on the uncomplexed general purpose polyimide polymer (comparative example 2). The glass transition point was also determined for the polyimide polymer produced by subjecting the polyimide precursor of the example 1 to a dehydration condensation reaction. The results are shown in Table 1.

TABLE 1

|  | | Example 1 | Comparative example 1 | Comparative example 2 | Polyimide (prior to complexing) |
|---|---|---|---|---|---|
| Glass transition point (° C.) | | 394 | 180 | 284 | 292 |
| Thermal decomposition temperature (10% mass loss) (° C.) | | 500 | 300 | 520 | 500 |
| Coefficient of linear thermal expansion (units: $10^{-4}$) | | 3.2 | 4.0 | 4.6 | 4.3 |
| Adhesion Tests (Cross cut peeling tests) | | | | | |
| Cu | Pre PCT | 100/100 | 22/100 | 0/100 | 0/100 |
|  | Post PCT | 100/100 | 0/100 | 0/100 | 0/100 |
| Silicon wafer | Pre PCT | 100/100 | 8/100 | 0/100 | 0/100 |
|  | Post PCT | 100/100 | 0/100 | 0/100 | 0/100 |

The results in Table 1 confirm that the composite material has a higher glass transition point and better heat resistance than the uncomplexed polyimide polymer. Furthermore, the adhesion of the composite material was also excellent. In addition, the coefficient of linear thermal expansion was small, and the variation in volume upon variations in temperature was also small.

Example 2

Figure 8:
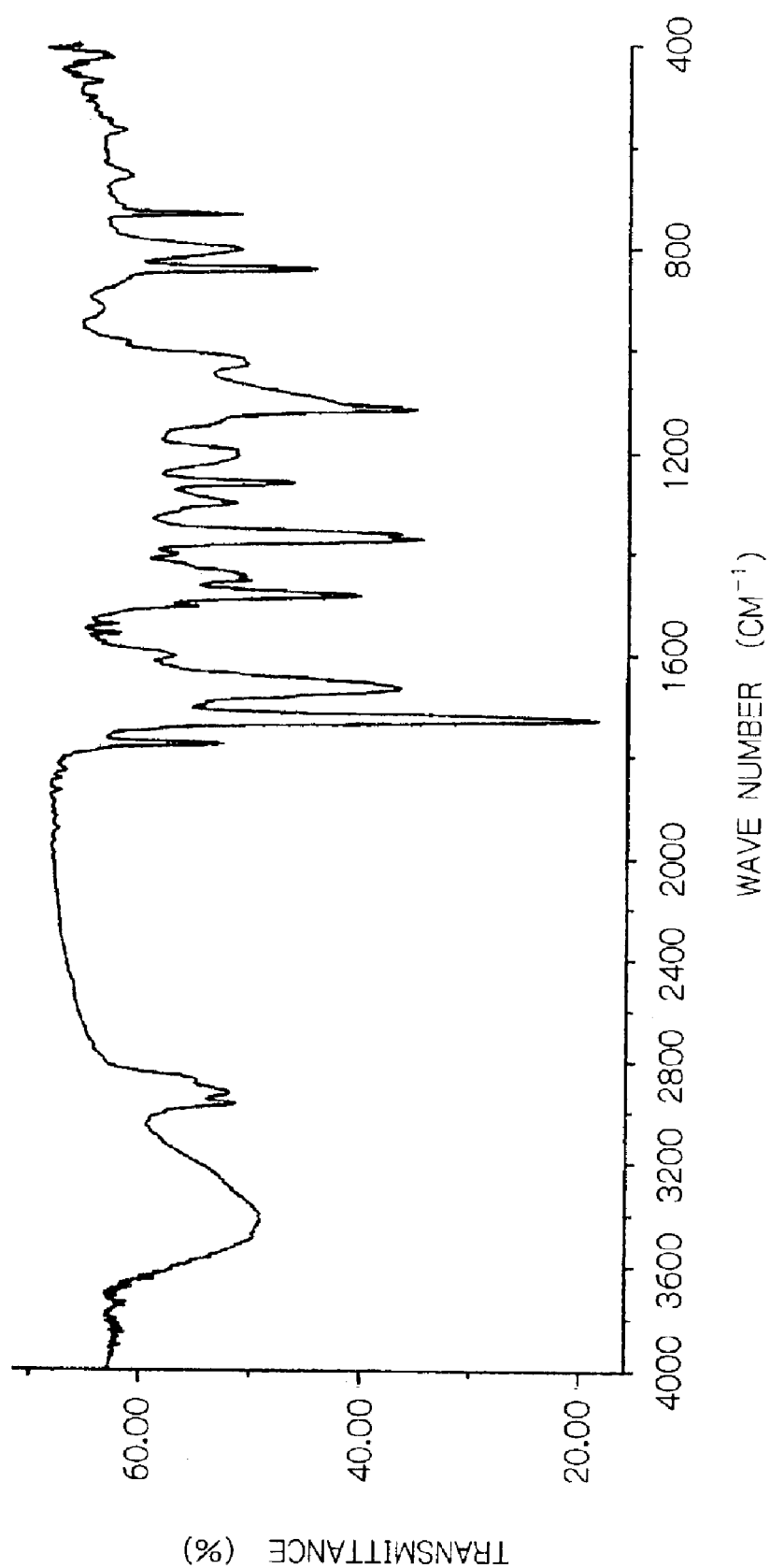
FIG. 8 is an IR spectrum of a product of an example 2.

Complexing of the Polyimide Precursor of Synthetic Example 5 and a Silicone Resin 2.0 g of a silicone resin (KF1001 (a brand name of Shin-Etsu Chemical Co., Ltd.) and 50 g of the polyimide precursor produced in the synthetic example 5 were mixed in a similar manner to the example 1, and 0.01 g of triphenylphosphine was then added as a catalyst, and the resulting mixture was reacted for 1 hour at 150° C. A sample was then extracted, and a flexibility test was conducted in the manner described below. The remaining reaction mixture was then reacted for a further 3 hours at 180° C. to complete the reaction, and following cooling, was poured into a large quantity of methanol. The precipitate that formed was filtered and dried and the resulting product was removed. The IR spectrum of the product is shown in FIG. 8. The formation of a complexed composite material was confirmed by the Si—O peak at 1000 to 1200 $cm^{-1}$. The mass average molecular weight of the composite material was 37,000. Measurement of the glass transition point in a similar manner to the example 1 produced a value of 260° C.
(Stress Measurement: Evaluation of Flexibility)

The polyimide precursor produced in the example 2 was spin coated on to a 5 inch silicon wafer, and then subjected to heat treatment for 3 hours at 180° C. to form a polyimide film. The radius of curvature of the 5 inch wafer was then measured, and the formula shown below was used to calculate the stress on the silicon wafer. In addition, as a comparative example 3, the polyimide precursor produced in the synthetic example 8 was also spin coated on to a 5 inch silicon wafer to form a polyimide film under the same conditions, and the radius of curvature of this 5 inch wafer was also measured, and the formula shown below was used to calculate the stress on the silicon wafer, in an identical manner. The results are shown in Table 2.

$$\sigma_f = \frac{t_s^2}{6 t_f R} \times \frac{E_S}{1 - r_s}$$

$\sigma_f$: generated stress (kg/mm$^2$)
$t_s$: silicon wafer thickness (μm)
$t_f$: film thickness (μm)
R: radius of curvature (μm)
$E_s$: Young's modulus for silicon wafer (dyne/cm$^2$)
$r_s$: Poisson's ratio for silicon wafer (no units)

TABLE 2

|  | Example 2 | Comparative example 3 |
|---|---|---|
| glass transition point (° C.) | 260 | 182 |
| generated stress (kg/mm$^2$) | 2.0 | 2.1 |
| film thickness | 10 | 10 |

From the results in Table 2, it is evident that a combination of low stress and a high glass transition point (heat resistance) has been achieved in the example 2. In contrast, in the comparative example 3, although a low stress was achieved, the siloxane units of the main skeleton have reduced the glass transition point, resulting in an unsatisfactory heat resistance.

Example 3

Figure 9:
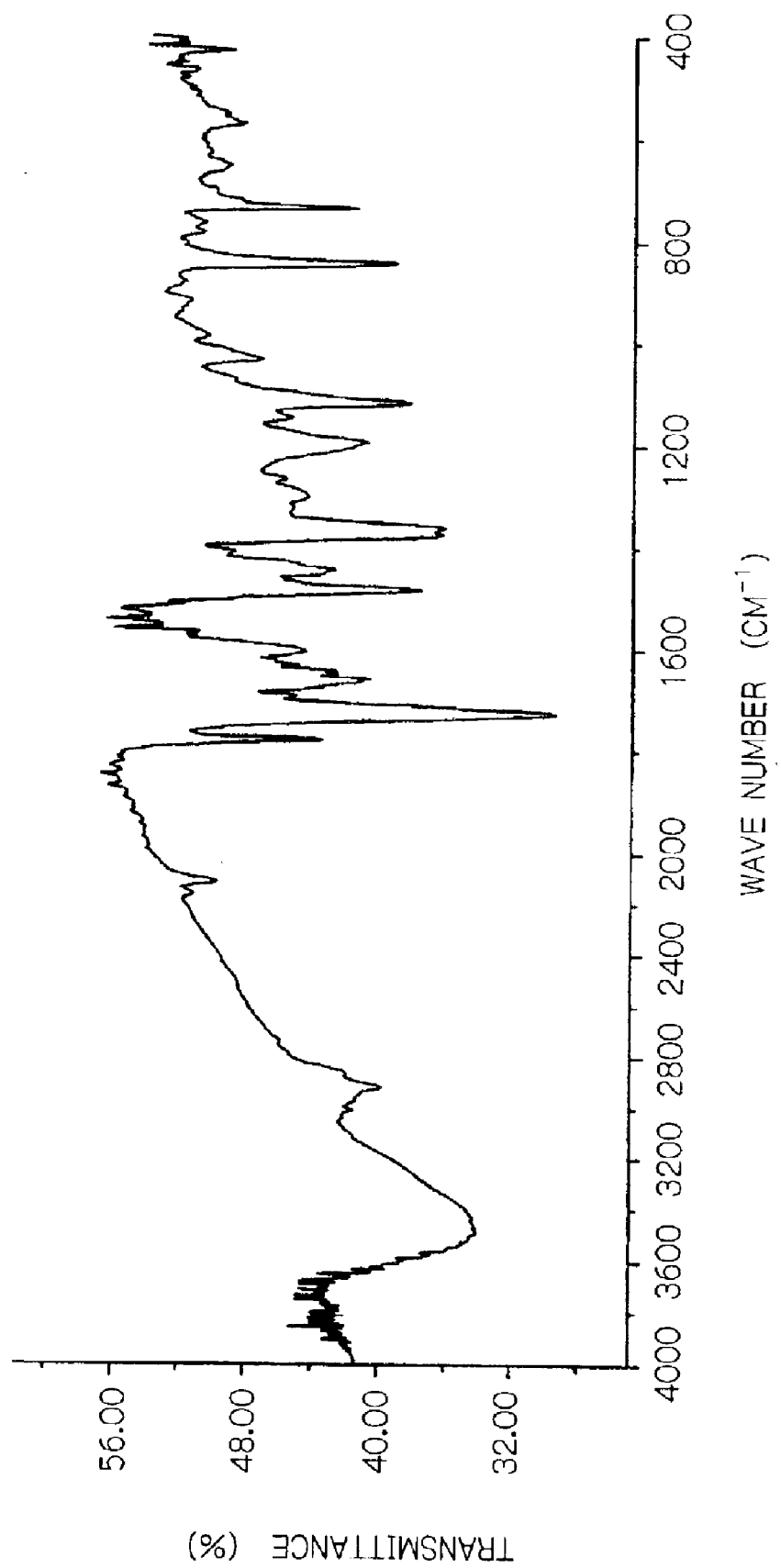
FIG. 9 is an IR spectrum of a product of an example 3.

Synthesis of a Photosensitive Polyimide polymer 26.7 g of the polyimide varnish produced in the synthetic example 6 was placed in a reaction vessel, 0.269 g of 1,2-naphthoquinone-2-diazide-5-sulfonyl chloride was added, and the mixture was stirred to produce a uniform mixture. With the reaction vessel cooled, 1.01 g of triethylamine diluted with acetone solvent to a concentration of 10 mass % was then added dropwise over a 30 minute period, and following completion of the addition, the reaction was permitted to proceed for 24 hours at room temperature. Following completion of the reaction, the reaction liquid was poured into 250 g of a 0.02 mass % aqueous oxalic acid solution, and the precipitated yellow colored solid was filtered, washed with ion exchange water, and then dried to yield a photosensitive polyimide polymer. The IR spectrum of this product is shown in FIG. 9. The IR spectrum confirmed that a photosensitive group had been introduced into the resin. 3.0 g of this photosensitive polyimide polymer was dissolved in 12 g of ethylcellosolve to prepare a 20 mass % solution. This photosensitive polyimide polymer solution was spin coated onto a silicon wafer, and following heating for 10 minutes on a 90° C. hot plate, the film thickness was measured and revealed a thickness of 5.2 μm. The film was then irradiated with 65 mJ/cm$^2$ of 365 nm radiation from a UV exposure device (ML-251C/A, manufactured by Ushio Inc.), subsequently immersed in a 1.98% aqueous TMAH solution (tetramethylammonium hydroxide) for 60 seconds, and then washed with water for 20 seconds. The film thickness of the exposed portion and the unexposed portion were measured, and a residual film ratio was determined. The results were 0% for the exposed portion and 100% for the unexposed portion.

As described above, according to the present invention, by using an amino group containing phenol derivative with a phenolic hydroxyl group, composite materials can be formed with other compounds, and a variety of materials can be provided which, while retaining the favorable characteristics of polyimide polymers, also display additional characteristics not obtainable using solely a polyimide.

What is claimed is:

1. An amino group containing phenol derivative represented by a general formula (1) show below:

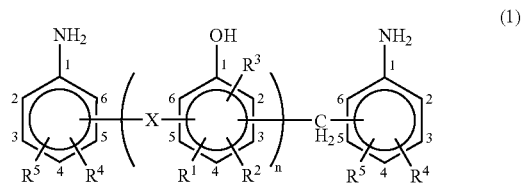

(wherein, $R^1$, $R^2$ and $R^3$, which may be identical or different, each represent an alkyl group of 1 to 9 carbon atoms, an alkoxy group of 1 to 10 carbon atoms, a COOR group (in which R represents an alkyl group of 1 to 6 carbon atoms) or a hydrogen atom; $R^4$ and $R^5$, which may be identical or different, each represent an alkyl group of 1 to 9 carbon atoms or a hydrogen atom; X represents —O—, —S—, —SO$_2$—, —C(CH$_3$)$_2$—, —CH$_2$—, —C(CH$_3$)(C$_2$H$_5$)—, or —C(CF$_3$)$_2$—; and n represents an integer of 1 or greater);

provided that when n is 2 and X is —CH$_2$—, the X group connecting the two phenol rings in the center of the compound is in the ortho orientation with respect to the OH group on both phenol rings.

2. An amino group containing phenol derivative according to claim 1, wherein said $R^4$ groups, said $R^5$ groups, and said X and —CH$_2$— groups bonded to respective terminal benzene rings are bonded to an identically numbered carbon atom in each case (numbers showing carbon atom position are shown in said general formula (1)).

3. An amino group containing phenol derivative according to claim 1, wherein X is a —CH$_2$— group.

4. An amino group containing phenol derivative according to claim 1, wherein $R^4$ and $R^5$ are methyl groups.

5. An amino group containing phenol derivative according to claim 1, wherein either one or two of $R^1$, $R^2$ and $R^3$ are hydrogen atoms, and a remainder are groups other than hydrogen atoms.

6. An amino group containing phenol derivative according to claim 5, wherein said groups other than hydrogen atoms are methyl groups.

7. An amino group containing phenol derivative according to claim 1, wherein all of $R^1$, $R^2$ and $R^3$ are methyl groups.

* * * * *